United States Patent [19]

Cooper et al.

[11] Patent Number: 4,721,510
[45] Date of Patent: Jan. 26, 1988

[54] ARTIFICIAL FOOT

[75] Inventors: John E. Cooper, Leatherhead; Alun Wilcox, Richmond, both of England

[73] Assignee: J. E. Hanger & Company, Limited, London, England

[21] Appl. No.: 17,725

[22] Filed: Feb. 24, 1987

[30] Foreign Application Priority Data

Feb. 28, 1986 [GB] United Kingdom ............... 8605026

[51] Int. Cl.⁴ .............................................. A61F 2/66
[52] U.S. Cl. ..................................................... 623/55
[58] Field of Search ...................................... 623/53-55

[56] References Cited

U.S. PATENT DOCUMENTS 3,766,569 10/1973 Orange ................................. 623/55
4,328,594 5/1982 Campbell et al. ................... 623/55

Primary Examiner—Richard J. Apley
Assistant Examiner—James Prizant
Attorney, Agent, or Firm—Shoemaker and Mattare, Ltd.

[57] ABSTRACT

A prosthetic foot comprises a hollow elastomeric cosmesis having a relatively large internal space, a keel of relatively stiff or rigid material, and a stiffener of glass reinforced plastics fitted between keel and instep region of the cosmesis. Front and rear snubbers extend from keel and front and rear stiffeners being portions of stiffener extend from under the keel with radiused ends resting on the sole of the cosmesis. During ambulation the stiffeners provide a primary path by which ground reaction is transmitted to the keel, but ground reaction bringing the stiffeners into contact with the snubbing means is transmitted to the keel via an overload path through the snubbing means.

15 Claims, 3 Drawing Figures

ARTIFICIAL FOOT

FIELD OF THE INVENTION

This invention relates to an artificial foot and to an artificial leg fitted with the artificial foot.

BACKGROUND TO THE INVENTION

When using an artificial leg, an amputee adapts his body movements to accommodate the characteristics of the components used in the prosthesis. This is done in such a way as to give the most desirable combination of motion, comfort and energy expenditure. Thus the body movements and gait of the amputee are directly related to the characteristics of the components used in the prosthesis. It follows therefore that by changing the characteristic of the components used in the prosthesis the gait of the amputee can be affected.

U.S. Pat. No. 4,547,913 (Phillips, assigned to Flex Foot Inc) describes a composite prosthetic foot having a leg portion, a foot portion and a heel portion all rigidly joined and all three provided with substantial elastic flexibility to provide return of energy absorbed and enable the amputee to engage in sports such as running and playing tennis.

SUMMARY OF THE INVENTION

An object of the invention is to provide a structure for an artificial foot in which heel and toe spring members respond to natural body movement in such a way that the gait of the amputee becomes close to normal. This is achieved by providing metatarsal and heel springs that store and release energy during usage in a manner that is consistent with normal body movements, thus giving a more lively, comfortable and less energy demanding action. It has been found that in springs based on composite material, the required mechanical and fatigue properties are achieved at dynamic load levels that are about 70–80% of the load to load failure. Such load levels are regularly exceeded by factors of three or four if, for example, the amputee jumps up and down, jumps off a chair or kicks the ground when recovering from a fall, although such excursions outside the normal loads of standing and walking are comparatively rare. Thus it is known that in addition to an ability to resist fatigue failure during several million walking cycles, a prosthetic foot should also be capable of withstanding a static load of about five times body weight (e.g. 5000 N for a man weighing 100 Kg). It is therefore desirable to provide additional paths for the overloads from jumping or similar events.

Accordingly the invention provides an artificial foot comprising in combination:

a hollow flexible cosmesis having a sole formed with an instep region and a region spaced from the instep region that flexes relative to the instep region during ambulation;

a keel member in the cosmesis having a lower region fixed to the sole at the instep region and having an upper region by which it is intended to be fixed to upper parts of the leg;

leaf spring means having a basal region held to the keel member at the instep region of the sole and having a terminal region that rests on the deformable region of the cosmesis; and snubbing means extending from the keel member in spaced overlying relationship to the leaf spring means, the arrangement being such that during ambulation the leaf spring means provides a primary path by which ground reaction is transmitted to the keel and that ground reaction causing the leaf spring means to contact the snubbing means is transmitted to the keel via an overload path through the snubbing means.

DESCRIPTION OF PREFERRED FEATURES

The region spaced from the instep region may be a metatarsal region of the sole, in which case preferably the leaf spring means terminates before a toe region of the foot so that at toe off the ground reaction is resisted only by flexion of the cosmesis, giving a transition in applied load with distance along the foot of the centre of ground reaction that mimics the change from metatarsal to toe region of the foot during normal walking. Preferably second leaf spring means and and snubbing means extend towards the heel of the cosmesis to provide load paths for ground reaction during the heel strike phase of ambulation, said heel being a second region of the cosmesis that flexes relative to the instep region during ambulation. To enable the amputee to stand stably the first and second leaf spring means are rated so that when the amputee is standing the centre of ground reaction is spaced from the heel by about one third of the length of the foot.

The performance of the foot is primarily dependant upon the load/deflection characteristics of the front and rear stiffness in the anterior/posterior plane but also depends upon the characteristics of the cosmesis. The design criteria for the stiffness may be derived from the movements of the shin, the ankle and the foot during normal locomotion which are all well known, as are the position along the foot from time to time of the centre of ground reaction forces. From this data it is possible to infer the deflections at different positions along the length of the foot which would give the same effective motion between the shin and the ground as would occur with a natural foot. These deflections, combined with ground reaction forces, serve to define the anterior/posterior plane characteristics that would comply with normal body movements.

BRIEF DESCRIPTION OF THE DRAWINGS

An embodiment of the invention will now be described, by way of example only, with reference to the accompanying drawings, in which.

DETAILED DESCRIPTION OF PREFERRED EMBODIMENTS

Figure 1:
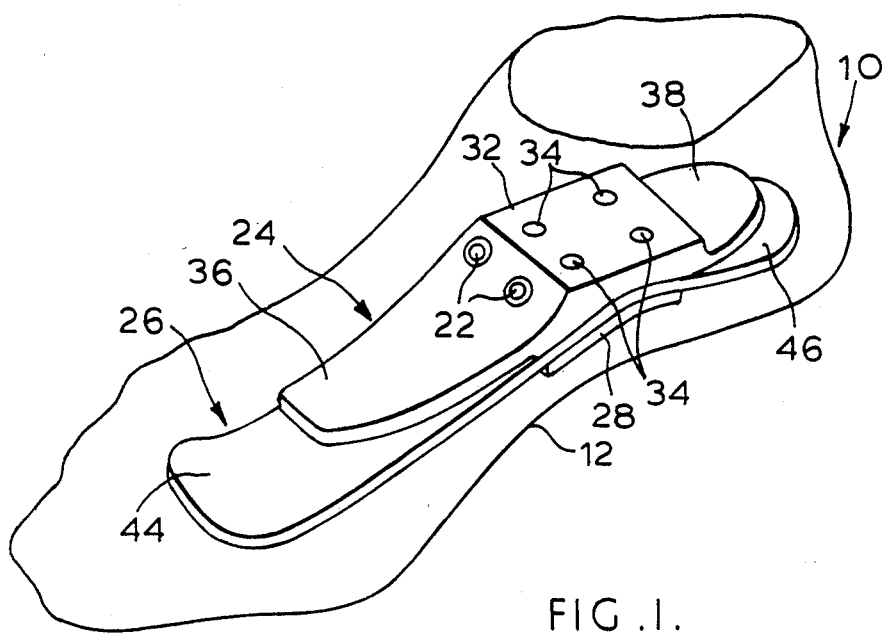
FIG. 1 is a diagrammatic perspective view of an artificial foot.
Figure 2:
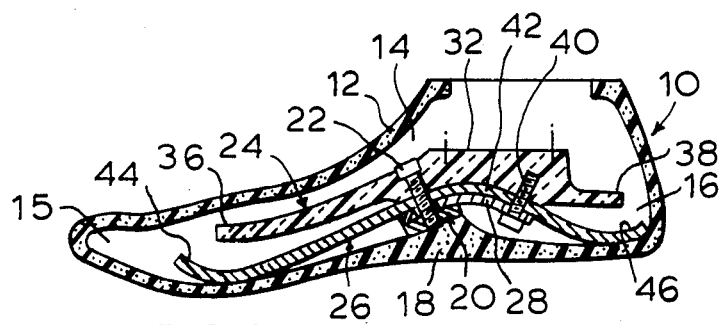
FIG. 2 is a view of the foot in longitudinal vertical section.

In the drawings, a prosthetic foot 10 comprises a hollow cosmesis 12 of elastomeric material such as a polyurethane foam in which the internal space 14 is relatively large and extends from the toe region 15 to the heel region 16 as shown. An instep region 18 of the sole of the foot is of increased thickness to define a wedge facing an anterior direction and has bonded thereto an anchoring plate 20. A pair of threaded holes in the plate 20 accept clamping screws 22 that pass respectively through an anterior region of a keel 24, stiffener 26 and instep reinforcement plate 28.

The keep 24 is of material such as continuous glass or other fibre-reinforced plastics or filled plastics that is made relatively stiff compared to the cosmesis 12 and stiffener 26 or is of inflexible material such as metal. It has a central region 32 formed in its top face with fixing holes 34 or other means by which the foot 10 can be attached to upper parts of the leg and is formed with anterior and posterior extensions defining a front snubber 36 and a rear snubber 38 that extend into the internal space 14 at a clearance from the sole of the foot. The instep plate 28 and stiffener 26 are clamped to the keel 24 from the underside by means of a pair of clamping screws 40. The stiffener 26 in side profile has a raised central region 42 that fits beneath the keel 24 and anterior and posterior regions that are spaced beneath the keel 24 to define a front stiffener 44 and a rear stiffener 46. The unsupported part of instep plate 28 and the screws 40 serve to clamp the central region of stiffener 26 to the keel 24 so that the rear portion 46 thereof that is free to flex relative to the keel 24 is short. The end of each stiffener 44, 46 is upwardly curved to define a radiused end that rests on the sole of the cosmesis as shown. The rear stiffener 46 extends to the keel region 16 and locates in a groove (not shown) therein to prevent it moving relatively to the cosmesis but the front stiffener 44 terminates at a metatarsus position short of the toe region 15. The stiffener 26 is formed in one piece from continuous glass or other fibre reinforced plastics material (glass filament reinforced plastics being preferred) and is made so as to be relatively flexible. The reinforcement plate 28 matches the curvature of the stiffener 26 in its region between screws 22, 40.

Figure 3:
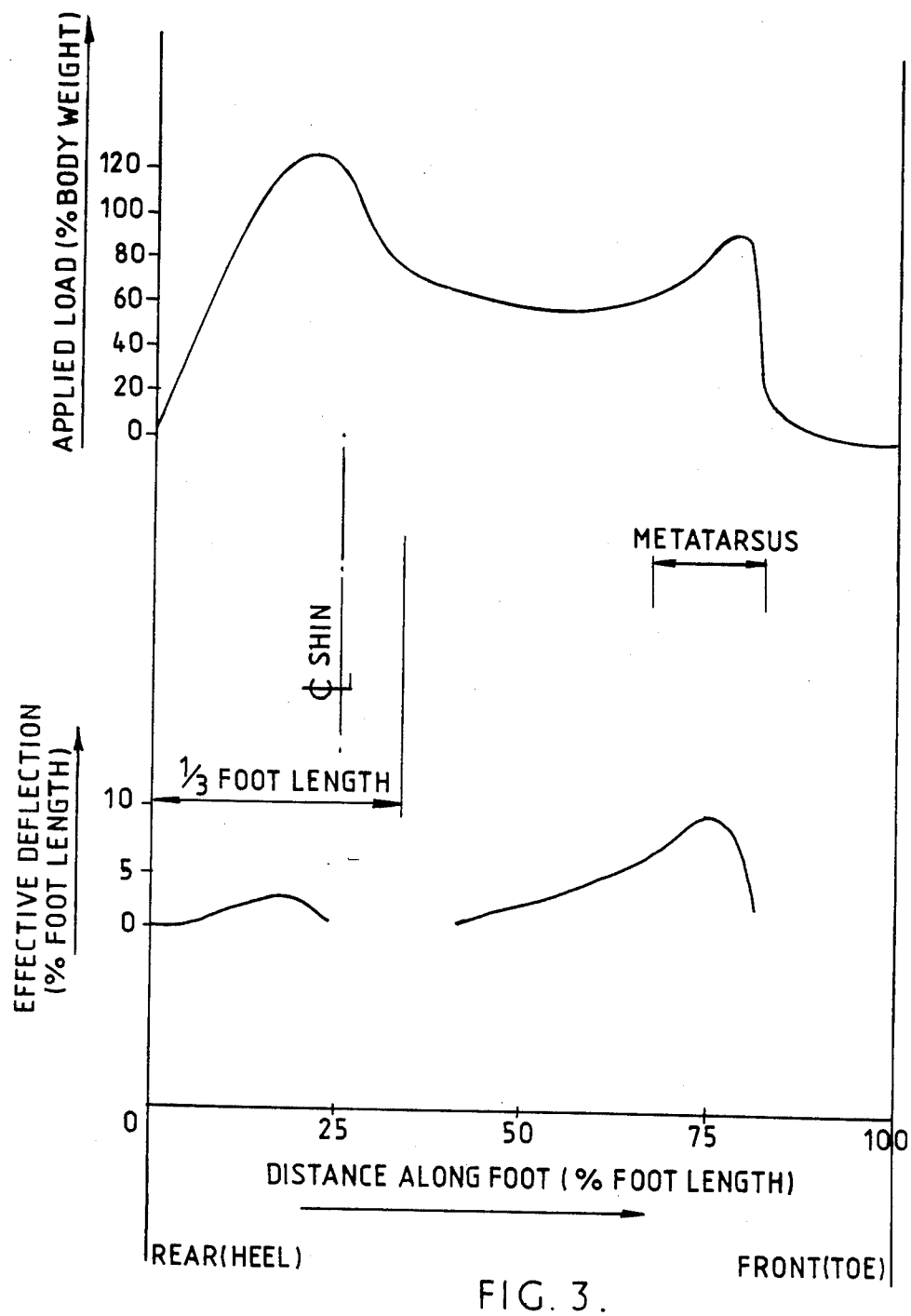
FIG. 3 is a graph of load and deflection against position of the centre of ground reaction along the foot.

The performance requirements of the foot are illustrated in FIG. 3 which shows the typical applied load and effective deflection for an amputee. It will be appreciated that the curves are based of nominal data and that individual amputees differ in their activity levels so that it may be necessary to provide alternative characteristics to meet their individual requirements. It will also be noted that FIG. 3 covers the period of initial heel contact and of toe off but not the time that both heel and toe are in contact simultaneously. At heel strike the rear stiffener 46 is the controlling component and at toe off the front stiffener 44 controls events, but for much of the load-bearing part of the walking cycle the load is distributed between the two stiffeners 44, 46. It is apparent from FIG. 3 that loads and deflections fall off very rapidly just ahead of the metatarsus. For this reason the front stiffener 44 terminates at that point and beyond that point the action required is provided by the elastic cosmesis 12. Between heel strike and toe off the characteristics required are a peak of relatively high reactive load but relatively small deflection towards the heel and a peak of relatively small reactive load but relatively high deflection adjacent the metatarsus region with an intervening plateau region.

The ends of the front and rear stiffeners 44, 46 are each radiused, as previously noted, for three reasons:

(a) to assist smooth transition at heel strike and toe off;

(b) to allow a range of different heel heights to be used, the characteristics illustrated in FIG. 3 being needed for heel heights of from 0 (flat foot) to 40 mm; and (c) to provide control over the position of the combined reaction of the front and rear stiffeners 44, 46 which is required while both front and rear stiffeners are under load, especially during standing where the centre of ground reaction should be spaced one third of the foot length from the heel to prevent toppling.

The stiffeners 44, 46 each deflect at least once per walking cycle: they are therefore critical in fatigue and are sized accordingly using an appropriate material. But the static strength requirement of the foot is many times greater than that required for normal activity and stiffeners 44, 46 designed for the loads, deflections and load cycle life appropriate to normal walking or more vigorous activity cannot by themselves meet the static load requirements. The front and rear snubbers 36, 38 are located at positions above the stiffeners 44, 46 such that contact therebetween occurs at a position where the stiffener has deflected a distance about equal to the peak deflection shown in FIG. 3 to establish a secondary load path from the sole of the cosmesis to upper parts of the leg. The secondary load path may be of one of two different kinds:

(a) for normal activity levels the snubber is of metal or other substantially rigid material and acts as a mechanical stop;

(b) for high activity levels the snubber acts as a spring so that after a nominal displacement the stiffener and snubber act in parallel, continuing to deflect and to provide a progressively increasing resistive load right up to the level of the static requirement, the stiffeners and snubbers both being sized to meet this level. In the high activity case the stiffener 44 or 46 and snubber 36, 38, which are both of reinforced plastics, may be made as a single component united at the centre. It will be appreciated that the design of a foot for a high level activity such as running is different from that primarily for a less strenuous activity such as walking.

It will be appreciated that the design of the stiffener and snubbers is related to the type and orientation of the filament. It has been found that glass fibre has a good combination of strength and deflection characteristic because of its relatively low elasticity.

The filament orientation is primarily unidirectional in the anterior-posterior plane with other directions used to give greater strength at the basal region.

The lateral cross-section of the stiffeners is designed to have low roll resistance to accommodate uneven surfaces and displacement in inversion/eversion.

It will be appreciated that modifications may be made to the embodiment described above without departing from the invention, the scope of which is defined in the appended claims. For example, although it is prepared to provide stiffeners and snubbers for both the metatarsal and the heel region, a foot could be made that had a stiffener and snubber for the metatarsal region combined with a simple region of resilient plastics foam located beneath the keel. The interior space 14 instead of being empty could be filled with a highly flexible low density plastics foam.

The foot of the invention may be used in association with a wide range of exoskeletal and endoskeletal artificial legs in place of a SACH or uniaxial foot and may be fitted, for example, to the applicant's ROELITE and ULTRA-ROELITE endoskeletal artificial legs.

We claim:

1. An artificial foot comprising in combination:
    a hollow flexible cosmesis having a sole formed with an instep region and a region spaced from the instep region that flexes relative to the instep region during ambulation;
    a keel member in the cosmesis having a lower region fixed to the sole at the instep region and having an upper region by which it is intended to be fixed to upper parts of the leg;

leaf spring means having a basal region held to the keel member at the instep region of the sole and having a terminal region that rests on the deformable region of the cosmesis; and snubbing means extending from the keel member in cantilevered relationship thereto, said snubbing means being spaced below said cosmesis and being in spaced overlying relationship to the leaf spring means which is deformable into contact with said snubbing means by ground reaction, the stiffness of the leaf spring means being such that during ambulation the leaf spring means provides a primary path by which ground reaction is transmitted to the keel and that ground reaction causing the leaf spring means to contact the snubbing means is transmitted to the keel via an overload path through the snubbing means.

2. A foot according to claim 1, wherein the cosmesis is formed of an elastomeric foam.

3. A foot according to claim 1, wherein the keel is attached to a plate bonded to the instep region of the sole which is of increased thickness.

4. A foot according to claim 1, wherein the keel member and snubbing means are of substantially rigid material so that the snubbing means acts as a mechanical stop for the leaf spring means.

5. A foot according to claim 4, wherein the keel member and snubbing means are of metal.

6. A foot according to claim 1, wherein the keel member and snubbing means are of stiffly flexible material such that after the leaf spring means has contacted the snubbing means the leaf spring means and the snubbing means act in parallel to provide a progressively increasing resistive load.

7. A foot according to claim 1, wherein the basal region of the leaf spring means is spaced above the sole.

8. A foot according to claim 7, wherein the terminal region of the leaf spring means is curved away from the sole to define a radiused tip of the leaf spring means.

9. A foot according to claim 1, wherein the leaf spring means is of filament reinforced plastics material.

10. A foot according to claim 9, wherein the filaments are of glass.

11. A foot according to claim 1, wherein the region spaced from the instep region is a metatarsal region of the sole.

12. A foot according to claim 11, wherein the leaf spring means terminates before a toe region of the foot whereby at toe off the ground reaction is resisted only by flexion of the cosmesis.

13. A foot according to claim 11, wherein second leaf spring means and second snubbing means extend towards the heel of the cosmesis to provide load paths for ground reaction during the heel strike phase of ambulation, said heel being a second region of the cosmesis that flexes relative to the instep region during ambulation.

14. A foot according to claim 13, wherein the first and second leaf spring means are rated so that when the amputee is standing the centre of ground reaction is spaced from the heel by about one third of the length of the foot.

15. An artificial leg fitted with a foot as claimed in claim 1.

* * * * *